US006303626B1

(12) United States Patent
Abramovici et al.

(10) Patent No.: US 6,303,626 B1
(45) Date of Patent: Oct. 16, 2001

(54) PHARMACEUTICAL FORMULATIONS IN DRY FORM FOR THE ORAL ADMINISTRATION OF A CYCLIC QUATERNARY AMMONIUM COMPOUND

(75) Inventors: Bernard Abramovici, Juvignac; Xavier Boulenc, Montpellier; Jean-Claude Gautier, Clapiers; Pol Vilain, Saussan, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/355,560

(22) PCT Filed: Feb. 17, 1998

(86) PCT No.: PCT/FR98/00299

§ 371 Date: Jul. 30, 1999

§ 102(e) Date: Jul. 30, 1999

(87) PCT Pub. No.: WO98/35663

PCT Pub. Date: Aug. 20, 1998

(30) Foreign Application Priority Data

Feb. 17, 1997 (FR) .................................................. 97 01826

(51) Int. Cl.⁷ .......................... A61K 31/14; A61K 31/46; A61K 9/16
(52) U.S. Cl. .......................... 514/305; 514/316; 514/323; 514/331; 546/135
(58) Field of Search .................................... 514/305, 316, 514/323, 331; 546/135

(56) References Cited

U.S. PATENT DOCUMENTS

| 5,340,822 | 8/1994 | Emonds-Alt et al. | 514/316 |
|---|---|---|---|
| 5,411,971 | 5/1995 | Emonds-Alt et al. | 514/318 |
| 5,641,777 | 6/1997 | Emonds-Alt et al. | 514/235.5 |
| 5,652,246 | 7/1997 | de Nanteuil et al. | 514/300 |
| 5,656,639 | 8/1997 | Emonds-Alt et al. | 514/305 |
| 5,665,886 | 9/1997 | Chabert et al. | 546/300 |
| 5,674,881 | 10/1997 | Emonds-Alt et al. | 514/329 |
| 5,679,693 | 10/1997 | Emonds-Alt et al. | 514/323 |
| 5,852,044 | 12/1998 | Gueudet et al. | 514/317 |

FOREIGN PATENT DOCUMENTS

| 0 512 901 | 11/1992 | (EP) . |
|---|---|---|
| 0 515 240 | 11/1992 | (EP) . |
| 0 559 538 | 9/1993 | (EP) . |
| 0 591 040 | 4/1994 | (EP) . |
| 0 708 101 | 4/1996 | (EP) . |
| 0 723 959 | 7/1996 | (EP) . |
| WO 95/26335 | 10/1995 | (WO) . |
| WO 95/26339 | 10/1995 | (WO) . |
| WO 96/06094 | 2/1996 | (WO) . |
| WO 96/12479 | 5/1996 | (WO) . |
| WO 96/23787 | 8/1996 | (WO) . |

*Primary Examiner*—Richard L. Raymond
(74) *Attorney, Agent, or Firm*—Michael D. Alexander; Paul E. Dupont

(57) ABSTRACT

The pharmaceutical formulations according to the invention contain from 0.5 to 50% by weight of a cyclic quaternary ammonium compound and pharmaceutically appropriate excipients and are formulated by wet granulation, preferably with polysorbate 80.

28 Claims, No Drawings

PHARMACEUTICAL FORMULATIONS IN DRY FORM FOR THE ORAL ADMINISTRATION OF A CYCLIC QUATERNARY AMMONIUM COMPOUND

The present application is a 371 of PCT/FR98/00299, filed Feb. 17, 1998.

The present invention relates to novel pharmaceutical formulations in dry form for oral administration, in which a cyclic quaternary ammonium compound is present as the active principle.

In particular, the invention relates to pharmaceutical formulations for oral administration which contain, as the active principle, a compound of the formula

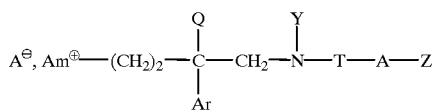

(I)

in which:
$AC^{\ominus}$ is a pharmaceutically acceptable anion;
$Am^{\oplus}$ is:
  i—either a group $Am_1^{\oplus}$ of the formula

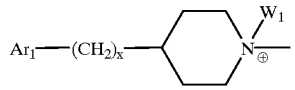

in which:
  $Ar_1$ is a phenyl which is unsubstituted or monosubstituted or polysubstituted by a substituent selected from a halogen atom, a hydroxyl. a $(C_1-C_4)$alkoxy, a $(C_1-C_4)$-alkyl and a trifluoromethyl, said substituents being identical or different;
  x is zero or one; and
  $W_1$ is a $(C_1-C_6)$alkyl or a benzyl group, the substituent $W_1$ being either in the axial position or in the equatorial position;
  ii—or a group $Am_2^{\oplus}$ of the formula

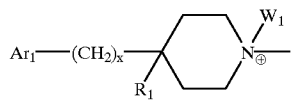

in which:
  $Ar_1$, x and $W_1$ are as defined above; and
  $R_1$ is a hydroxyl, a $(C_1-C_4)$alkoxy, a formyloxy, a $(C_1-C_3)$alkylcarbonyloxy, a carboxyl, a $(C_1-C_4)$alkoxycarbonyl, a cyano, a $((C_1-C_3)$alkylcarbonylamino, a mercapto or a $(C_1-C_4)$alkylthio;
  iii—or a group $Am_3^{61}$ of the formula

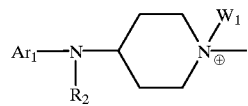

in which:
  $Ar_1$ and $W_1$ are as defined above; and
  $R_2$ is hydrogen, a $(C_1-C_3)$alkyl or a $(C_1-C_3)$alkylcarbonyl;
  iv—or a group $Am_4^{\oplus}$ of the formula

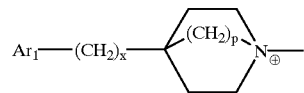

in which:
  $Ar_1$ and x are as defined above; and
  p is one or two;
  v—or a group $Am_5^{\oplus}$ of the formula

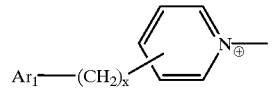

in which:
  $Ar_1$ and x are as defined above.
  Ar is a phenyl which is unsubstituted or monosubstituted or disubstituted by a substituent selected from a halogen atom, a $(C_1-C_3)$alkoxy, a $(C_1-C_3)$alkyl and a trifluoromethyl, said substituents being identical or different; a naphthyl; or an indolyl;
  Q and Y have one of the following groups of meanings:
    a) $Q_1$ and $Y_1$;
    b) $Q_2$ and $Y_2$ when $Am^{\oplus}$ is a group $Am_1^{\oplus}$, $Am_2^{\oplus}$, $Am_4^{\oplus}$ or $Am_5^{\oplus}$;
    c) $Q_3$ and $Y_3$ when $Am^{\oplus}$ is a group $Am_1^{\oplus}$ or $Am_2^{\oplus}$ or a group $Am_4^{\oplus}$ in which $Ar_1$ is a phenyl and p is two;
    d) $Q_4$ and $Y_4$ when $Am^{\oplus}$ is a group $Am_1^{\oplus}$, $Am_3^{\oplus}$, $Am_4^{\oplus}$ or $Am_5^{\oplus}$;
  $Q_1$ is hydrogen;
  $Y_1$ is hydrogen, a $(C_1-C_4)$alkyl, an $\omega-(C_1-C_4)$alkoxy-$(C_2-C_4)$alkylene, an $\omega-(C_1-C_4)$alkylcarbonyloxy-$(C_2-C_4)$alkylene, an $\omega$-benzoyloxy-$(C_2-C_4)$alkylene, an $\omega$-hydroxy-$(C_2-C_4)$alkylene, an $\omega-(C_1-C_4)$alkylthio-$(C_2-C_4)$alkylene, an $\omega-(C_1-C_4)$-alkylcarbonyl-$(C_2-C_4)$alkylene, an $\omega$-carboxy-$(C_2-C_4)$alkylene, an $\omega-(C_1-C_4)$-alkoxycarbonyl-$(C_2-C_4)$alkylene, an co-benzyloxy-$(C_2-C_4)$alkylene, an $\omega$-formyl-oxy-$(C_2-C_4)$alkylene, an $\omega-R_3NHCOO-(C_2-C_4)$alkylene, an $\omega-R_4R_5NCO-(C_2-C_4)$-alkylene, an $\omega-R_6CONR_7-(C_2-C_4)$alkylene, an $\omega-R_8OCONR_7-(C_2-C_4)$alkylene, an $\omega-R_4R_5NCONR_7-(C_2-C_4)$alkylene, an $\omega-R_9SO_2NR_7-(C_2-C_4)$alkylene, an $\omega$-cyano-$(C_1-C_3)$alkylene;
  $Q_2$ and $Y_2$ together form an ethylene, trimethylene or tetramethylene group;
  $Q_3$ and $Y_3$ together form a group

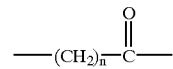

in which n is one, two or three;
  $Q_4$ and $Y_4$ together form a radical selected from:
    $A_1$) —O—$CH_2$—
    $A_2$) —O—CO—
    $A_3$) —$CH_2$—O—CO—
    $A_4$) —O—$CH_2$—CO—
    $A_5$) —O—$CH_2$—$CH_2$—
    $A_6$) —N($R_{10}$)—CO—
    $A_7$) —N($R_{10}$)—CO—CO—
    $A_8$) —N($R_{10}$)—$CH_2$—$CH_2$—

T is either a group —CO— when Q and Y are $Q_1$ and $Y_1$, $Q_2$ and $Y_2$ or $Q_4$ and $Y_4$ when they together form a radical $A_1$), $A_5$) or $A_8$); or a group —CH$_2$— when Q and Y are $Q_3$ and $Y_3$ or $Q_4$ and $Y_4$ when they together form a radical $A_2$), $A_3$), $A_4$), $A_6$) or $A_7$);

A is either a direct bond or a methylene group when T is —CO—, or a direct bond when T is —CH$_2$—;

Z is:
- a phenyl which is unsubstituted or monosubstituted or polysubstituted by a substituent selected from a halogen atom; a trifluoromethyl; a cyano; a hydroxyl; a nitro; an amino which is unsubstituted or monosubstituted or polysubstituted by a $(C_1-C_4)$ alkyl; a benzylamino; a carboxyl; a $(C_1-C_{10})$alkyl; a $(C_3-C_7)$cycloalkyl which is unsubstituted or monosubstituted or polysubstituted by a methyl; a $(C_1-C_{10})$alkoxy; a $(C_3-C_7)$cycloalkoxy which is unsubstituted or monosubstituted or polysubstituted by a methyl; a mercapto; a $(C_1-C_{10})$alkylthio; a $(C_1-C_6)$alkylcarbonyloxy; a $(C_1-C_6)$ alkylcarbonylamino; a benzoylamino; a $(C_1-C_4)$ alkoxycarbonyl; a $(C_3-C_7)$cycloalkylcarbonyl; a carbamoyl which is unsubstituted or monosubstituted or disubstituted by a $(C_1-C_4)$alkyl; a ureido which is unsubstituted or monosubstituted or disubstituted in the 3-position by a $(C_1-C_4)$alkyl or a $(C_3-C_7)$ cycloalkyl; and a (pyrrolidin-1-yl)carbonylamino, said substituents being identical or different;
- a naphthyl which is unsubstituted or monosubstituted or polysubstituted by a halogen, a trifluoromethyl, a $(C_1-C_4)$alkyl, a hydroxyl or a $(C_1-C_4)$alkoxy;
- a pyridyl; a thienyl; an indolyl; a quinolyl; a benzothienyl; an imidazolyl;

$R_3$ is a $(C_1-C_7)$alkyl or a phenyl;

$R_4$ and $R_5$ are each independently a hydrogen or a $((C_1-C_7)$alkyl; $R_5$ can also be a $(C_3-C_7)$cycloalkyl, a $(C_3-C_7)$cycloalkylmethyl, a phenyl or a benzyl; or $R_4$ and $R_5$, together with the nitrogen atom to which they are bonded, form a heterocycle selected from azetidine, pyrrolidine, piperidine, mnorpholine, thiomorpholine, perhydroazepine and piperazine which is unsubstituted or substituted in the 4-position by a $(C_1-C_4)$alkyl;

$R_6$ is a hydrogen, a $(C_1-C_7)$alkyl, a vinyl, a phenyl, a benzyl, a pyridyl or a $(C_3-C_7)$cycloalkyl which is unsubstituted or substituted ty one or more methyls;

$R_7$ is a hydrogen or a $(C_1-C_7)$alkyl;

$R_8$ is a $(C_1-C_7)$alkyl or a phenyl;

$R_9$ is a $(C_1-C_7)$alkyl; an amino which is unsubstituted or substituted by one or two $(C_1-C_7)$alkyls; a phenyl which is unsubstituted or monosubstituted or polysubstituted by a substituent selected from a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$alkylcarbonyloxy, a cyano, a nitro and an amino which is unsubstituted or substituted by one or two $(C_1-C_7)$alkyls, said substituents being identical or different;

$R_{10}$ is hydrogen or a $(C_1-C_4)$alkyl, and its optional salts with mineral or organic acids and their optional solvates.

The compounds of formula (I) which are useful for the invention include both the racemates and the optically pure isomers, as well as the axial and equatorial isomers when Ams in the compound of formula (I) is a group $Am_1^{\oplus}$, a group $Am_2^{\oplus}$ or a group $Am_3^{\oplus}$.

The compounds of formula (I) are described in patent applications FP-A-0 512 901, EP-A-0 515 240, EP-A-0 559 538, EP-A-0 591 040, WO 95/26 339, EP-A-0 700 382, EP-A-0 723 959 and WO 96/23 787.

Among the compounds of formula (I), those of the formula

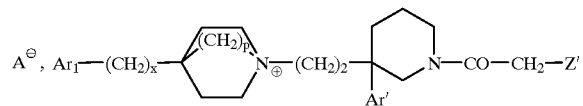

in which:
- $Ar_1$, x and p are as defined for a compound of formula (I);
- Ar' is a 3,4-dichlorophenyl or a 3,4-difluorophenyl;
- Z' is a phenyl substituted in the 3-position by a halogen or a $(C_1-C_{10})$alkoxy;
- $A^{\ominus}$ is a pharmaceutically acceptable anion, are preferred for the invention.

More particularly, the invention relates to pharmaceutical formulations in dry forms for the oral administration of (S)-1-{2-[3-(3,4-dichlorophenyl)-1-(3-isopropoxyphenylacetyl)piperidin-3-yl]ethyl}-4-phenyl-1-azoniabicyclo[2.2.2]octane, or SR 140333, of the formula

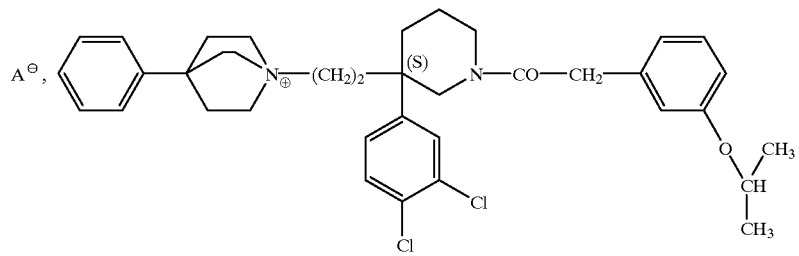

in which $A^{\ominus}$ is a pharmaceutically acceptable anion.

The benzenesulfonate of SR 140333, hereafter called compound A, is very particularly preferred. The international non-proprietary name of this compound is nolpitantium besilate.

The compounds of formula (1) have been described as antagonists of substance P, which is the natural ligand of the $NK_1$ receptors and hence have an affinity for the said receptors. For oral administration, such compounds must have a good absorption which entails both a good solubility in aqueous media and a good capacity to pass through the intestinal membrane (M. Rowland and T. N. Tozer in Clinical pharmacokinetics, concepts and applications, published by Lea and Fehiger, 1989, 2nd edition, pp. 113–130).

The solubility of the compounds of formula (I) has been studied in different media: their solubility in water is generally below 5 mg/ml, but they are soluble in hydrophilic solvents such as alcohols or glycols.

Being quaternary ammonium compounds, the compounds of formula (I) remain in ionized form irrespective of the pH of the medium in which they are present, especially at neutral pH, which is the pH of the intestinal medium.

It is known that ionic compounds, especially quaternary ammonium compounds, cannot easily pass through the epithelial membranes (J. P. Labaune in Pharmacocinétique, Principes fondamentaux, published by Masson, 1988, 2nd edition, pp. 7–33).

The cell line Caco-2 has the particular characteristic of exhibiting differentiation in vitro to form an epithelial monolayer. This line is conventionally used for evaluating the ability of compounds to permeate the epithelium (Crit. Rev. Ther. Drug Carrier System. 1991, 8 (4), 105–330).

In this model, the permeability to compound A dissolved in dimethyl sulfoxide (DMSO) is $3.4.10^{-7}$ cm/s. Furthermore, studies performed on the rat with a 0.6% aqueous solution of compound A in methyl cellulose have shown that its estimated absorption is less than 1%.

Non-ionic surfactants and absorption promoters have been tested in order to find out their effect on the ability of a compound of formula (I) to permeate membranes. These products have not shown any positive effects.

The compounds of formula (I) also have other physicochemical properties which make them difficult to formulate. Thus the low density of the compounds of formula (I) is poorly compatible with their formulation simply by dry mixing. Furthermore, as they are highly electrostatic, these compounds tend to stick to surfaces, which detracts from possible compression processes.

As far as compound A is concerned, it crystallizes in the form of needles and its strong electrostatic character results in the formation of aggregates. Furthermore, micronization of the product would be potentially dangerous because of the risk of explosion due to the accumulation of charges.

Thus, to develop a galenic formulation for the compounds of formula (I), it is necessary both to overcome their very low solubility and their poor passage through membranes, and to achieve a formulation which is compatible with the preparation of dry forms.

It has now been found that a pharmaceutical formulation, presented in dry form, for the oral administration of a compound of fonnula (I) can be prepared by using wet granulation to formulate the product; such pharmaceutical formulations make it possible both to avoid the accumulation of electrical charges and to improve the bioavailability of the active principle.

Wet granulation is understood as meaning the pharmaceutical operation which makes it possible, with the aid of a granulating liquid, to densify a mixture of powders containing the active principle, said mixture constituting the internal phase of the formulation, the resulting wet mass being dried and then graded prior to the addition of the ingredients constituting the external phase of said formulation.

In particular, the present invention relates to pharmaceutical formulations comprising from 0.5 to 50% by weight of the compound of formula (I) and pharmaceutically acceptable excipients, said formulations being produced by wet granulation.

Thus the formulations of the invention contain the following ingredients, expressed as percentages of the total weight of the formulation:

| | |
|---|---|
| active principle | 0.5 to 50% |
| binder | 1 to 10% |
| disintegrating agent | 0 to 10% |
| antiadhesive | 0 to 5% |
| lubricant | 0.2 to 5% |
| flow promoter | 0 to 15% |
| polysorbate 80 | 0 to 20% |
| color | 0 to 2% |
| flavoring | 0 to 2% |
| diluent in sufficient amount (QS) for 100%. | |

Surprisingly, it has been observed that the addition of one particular polysorbate, namely polysorbate 80, to a solution of compound A in the cell culture medium substantially improves the transepithelial passage in the Caco-2 model.

The pharmaceutical formulations according to the invention preferably contain from 10 mg to 100 mg of polysorbate 80 per dosage unit. More particularly, the pharmaceutical formulations according to the invention contain from 15 mg to 60 mg of polysorbate 80 per dosage unit.

The pharmaceutical formulations according to the present invention can be presented in the form of gelatin capsules, tablets, sachets or powders.

It is also possible to prepare enteric formulations for pharmaceutical compositions in the form of gelatin capsules or tablets.

Such formulations are used to protect the active principle from the strong acidity in the stomach. Such formulations are prepared by coating the gelatin capsule or tablet with a polymer film which is insoluble in an acid environment and soluble in a basic environment.

The diluent used in the composition of the present invention can be one or more compounds which are capable of densifying the active principle to give the desired mass. The preferred diluents are mineral phosphates such as calcium phosphates; sugars such as hydrated or anhydrous lactose, or mannitol; and cellulose or cellulose derivatives, for example microcrystalline cellulose, starch, corn starch or pregelatinized starch. Very particularly preferred diluents are lactose monohydrate, mannitol, microcrystalline cellulose and corn starch, used by themselves or in a mixture, for example a mixture of lactose monohydrate and corn starch or a mixture of lactose monohydrate, corn starch and microcrystalline cellulose.

The binder employed in the composition of the present invention can be one or more compounds which are capable of densifying a compound of formula (I), converting it to coarser and denser particles with better flow properties. The preferred binders are alginic acid or sodium alginate; cellulose and cellulose derivatives such as sodium carboxymethyl cellulose, ethyl cellulose, hydroxyethyl cellulose, hydroxypropyl cellulose, hydroxypropyl methyl cellulose or methyl cellulose, gelatin; acrylic acid polymers; and povidone, for example povidone K-30; hydroxypropyl methyl cellulose and povidone K-30 are very particularly preferred binders.

The disintegrating agent employed in the composition of the present invention can be one or more compounds which facilitate the disintegration of the prepared formulation when it is placed in an aqueous medium. The preferred disintegrating agents are cellulose or cellulose derivatives such as sodium carboxymethyl cellulose, crosslinked sodium carboxymethyl cellulose, micro-crystalline cellulose, cellulose powder, crospovidone; pregelatinized starch, sodium starch glyconate, sodium carboxymethyl starch, or starch. Crospovidone, crosslinked sodium carboxymethyl cellulose and sodium carboxymethyl starch are preferred disintegrating agents.

The antiadhesive employed in the composition of the present invention can be one or more compounds which are capable of reducing the sticky character of the formulation, for example of preventing adhesion to metal surfaces. The preferred antiadhesives are compounds containing silicon, for example silica or talcum.

The flow promoter employed in the composition of the present invention can be one or more compounds which are capable of facilitating the flow of the prepared formulation. The preferred flow promoters are compounds containing silicon, for example anhydrous colloidal silica or precipitated silica.

The lubricant employed in the composition of the present invention can be one or more compounds which are capable of preventing the problems associated with the preparation of dry forms, such as the sticking and/or seizing problems which occur in the machines during compression or filling. The preferred lubricants are fatty acids or fatty acid derivatives such as calcium stearate, glyceryl monostearate, glyceryl palmitostearate, magnesium stearate, sodium laurylsulfate, sodium stearylfumarate, zinc stearate or stearic acid; hydrogenated vegetable oils, for example hydrogenated castor oil; polyalkylene glycols or polyethylene glycol; sodium benzoate; or talcum. Magnesium stearate or sodium stearylfumarate is preferred according to the present invention.

The color employed in the formulation of the present invention can be one or more compounds which are capable of imparting the desired color to the prepared formulation. The addition of a color can serve for example to differentiate between formulations containing different doses of active principle. The preferred colors are iron oxides.

Examples of enteric coating films which may be mentioned are cellulose acetophthalate, polyvinyl acetophthalate, hydroxypropyl methyl cellulose phthalate or methacrylic acid copolymers.

Examples of methacrylic acid copolymers which may be mentioned are the type C methacrylic acid copolymer marketed under the trade mark EUDRAGIT® L30 D-55 by ROHM, or the ethyl acrylate/methacrylic acid copolymer marketed under the trade mark KOLLICOAT® MAE 30D by BASF.

The elasticity of the coating film can be increased by adding plasticizers such as a polyethylene glycol, 1,2-propylene glycol, clibutyl phthalate or a citrate.

In certain cases, in particular when preparing enteric formulations with gelatin capsules, it may be preferable to cover the gelatin capsule with a film coating consisting of a precoating before the enteric coating. The precoating can be made, for example, of hydroxypropyl cellulose, povidone or a methacrylic acid copolymer in association with appropriate excipients.

According to the present invention, the pharmaceutical formulations are prepared by a wet granulation process wherein:
  a) for the internal phase, the active principle, the diluent, optionally the binder, optionally the polysorbate 80, and optionally the color are mixed at room temperature;
  b) the mixture is wetted with purified water as the granulating liquid;
  c) the resulting wet mass is dried and then graded; and
  d) the ingredients of the external phase, namely the lubricant, the disintegrating agent. the antiadhesive, the flow promoter and, optionally the color and/or the flavoring, are added to the graded dry grains obtained.

According to the present invention, one particular embodiment consists in incorporating the polysorbate 80 into the purified water in order to carry out the wet granulation.

In another particular embodiment, the binder is incorporated into the purified water in order to carry out the wet granulation.

When preparing enteric formulations, the film coating of a gelatin capsule or tablet according to the invention can contain a coating film of the following weight composition:

| Coating: | |
| --- | --- |
| type C methacrylic acid copolymer | 54.8% |
| glycerol | 3.3% |
| polysorbate 80 in 33% solution | 0.7% |
| water | 41.2%. |

For the film coating of enteric gelatin capsules, they are preferably first precoated with a film of the following weight composition:

| Precoating: | |
| --- | --- |
| type C methacrylic acid copolymer | 46.6% |
| glycerol | 4.6% |
| polysorbate 80 in 33% aqueous solution | 4.6% |
| water | 44.2% |

More particularly, the present invention relates to a pharmaceutical formulation for the oral administration of a compound of formula (I) which

| contains the following by weight | |
| --- | --- |
| active principle | 0.5 to 20% |
| binder | 2.5 to 6% |
| disintegrating agent | 0 to 5% |
| antiadhesive | 0 to 3% |
| lubricant | 0.5 to 3% |
| flow promoter | 0 to 5% |
| polysorbate 80 | 0 to 20% |
| color | 0 to 2% |
| flavoring | 0 to 2% |
| diluent in sufficient amount (QS) for 100%. | |

In one particular embodiment, the present invention relates to a pharmaceutical formulation for oral administration which contains the following by weight:

| compound A | 0.5 to 10% |
| --- | --- |
| lactose monohydrate | 60 to 80% |
| corn starch | 15 to 25% |
| povidone K-30 | 2 to 5% |
| polysorbate 80 | 0 to 20% |
| magnesium stearate | 1%. |

Preferably, the pharmaceutical compositions according to the invention contain from 10 to 100 mg and more particularly from 15 mg to 60 mg of polysorbate 80 per dosage unit. In one preferred embodiment, this compound is added with the water for granulation.

Thus the present invention relates very particularly to the pharmaceutical formulations for the oral administration of a compound A which have one of the following formulations:

i) in the internal phase:

| | |
|---|---|
| compound A | 0.7% |
| lactose monohydrate | 75.3% |
| corn starch | 20% |
| povidone K-30 | 3% |
| purified water for wet granulation QS | | in the external phase:

| | |
|---|---|
| magnesium stearate | 1%. | ii) in the internal phase:

| | |
|---|---|
| compound A | 7.9% |
| lactose monohydrate | 68.1% |
| corn starch | 20% |
| povidone K-30 | 3% |
| purified water for wet granulation QS | | in the external phase:

| | |
|---|---|
| magnesium stearate | 1%. | iii) in the internal phase:

| | |
|---|---|
| compound A | 3.1% |
| lactose monohydrate | 66.6% |
| corn starch | 20% |
| povidone K-30 | 3% |
| purified water for wet granulation QS | |
| polysorbate 80 | 6.3% | in the external phase:

| | |
|---|---|
| magnesium stearate | 1%. |

In this last formulation, the polysorbate 80 can be incorporated into the water for granulation.

The characteristics and advantages of the above compositions will become apparent from the following description based on the compositions given as Examples.

TESTS

1. Solubility of Compound A

The solubility in water was measured at the saturation point, after 24 hours. at room temperature; the measurements were made by UV spectrometry at $\lambda=275$ nm after calibration in an ethanolic solution.

| pH | 1 | 3 | 5 | 7 | 9 |
|---|---|---|---|---|---|
| Concentration of compound A mg/ml | 0.31 | 0.31 | 0.31 | 0.29 | 0.31 |

It is clear that this solubility is low and not dependent on the pH.

Compound A is also soluble in dimethyl sulfoxide (DMSO) in an amount of 168 mg/ml.

2. Evaluation of the Intestinal Transepithelial Passage of Compound A

Caco-2 cells are inoculated onto microporous polycarbonate filters covered with collagen. The cellular monolayer formed on the filter then makes it possible to separate an apical compartment (imitating the intestinal lumen) from a basal compartment (imitating the blood circulation).

The composition containing the compound to be studied is then placed on the apical side and the passage of this compound, dispersed or solubilized in Hank's medium, through this cellular barrier is evaluated by measuring the kinetics of its appearance on the basal side. This aqueous medium, of pH 6.5, has the following composition: NaCl=8.0 g/l; KCl=0.4 g/l; $CaCl_2$=0.19 g/l; $MgCl_2$=0.1 g/l; $MgSO_4$=0.1 g/l; $Na_2HPO_4$=0.09 g/l; $KH_2PO_4$=0.06 g/l; $NaHCO_3$=0.35 g/l; glucose=1 g/l; phenol red=0.01 g/l.

The transepithelial passage of formulation 1 below, produced by wet granulation according to the invention, was studied:

| Formulation 1 | |
|---|---|
| compound A | 0.7% |
| lactose monohydrate | 75.3% |
| corn starch | 20% |
| povidone K-30 | 3% |
| magnesium stearate | 1%. |

In the Caco-2 model, the rate of passage of compound A in formulation 1 is 3 times as great as that of compound A in suspension in the cell culture medium. Thus, by virtue of formulation 1, the rate of passage of compound A is similar to that measured when compound A is in solution in DMSO, so formulation 1 makes it possible totally to rectify the low solubility characteristic of compound A.

Various non-ionic surfactants or agents said to improve absorption, such as a $C_8$–$C_{10}$ fatty acid or one of its derivatives, were added to the formulation described above, placed in Hank's medium, and the relative rate of intestinal transepithelial passage of compound A in these formulations was measured.

| Formulation | Concentration of the agent added (mg/l) | Relative rate of transport |
|---|---|---|
| Formulation 1 | 0 | 1 ± 0.20 |
| 1 + polysorbate 60 | 100 | 0.51 ± 0.22 |
| | 200 | 0.62 ± 0.15 |
| 1 + polysorbate 80 | 100 | 2.77 ± 1.53 |
| | 200 | 4.39 ± 0.25 |
| 1 + Cremophor ® RH 40 | 100 | 0.66 ± 0.40 |
| | 200 | 0.51 ± 0.18 |
| 1 + Synperonic ® 44 | 100 | 0.92 ± 0.10 |
| | 200 | 1.48 ± 0.24 |
| 1 + Synperonic ® 127 | 100 | 0.85 ± 0.06 |
| | 200 | 1.19 ± 0.17 |
| 1 + Span ® 20 | 100 | 0.73 ± 0.48 |
| | 200 | 0.60 ± 0.28 |
| 1 + caprylic acid | 100 | 0.39 ± 0.03 |
| | 200 | 0.34 ± 0.01 |
| 1 + monocapryloylglycerol | 100 | 0.27 ± 0.06 |
| | 200 | 0.56 ± 0.11 |

In the various formulations studied, as the compound A is dissolved by the constituents of formulation 1, it is indeed the effect of the effect of the different agents on the absortion of compound A which is measured.

Only polysorbate 80 (100 and 200 mg/l), added to formulation 1, causes a notable increase in the rate of transport of compound A, whereas the other non-ionic surfactants or the absorption promoters either have no effect or reduce the rate of transport.

It was proved that polysorbate 80 causes no deterioration of the epithelial membrane up to a high concentration (4800 mg/l).

According to literature data, the intestinal volume is about 250 ml (J. B. Dressman et al., J. Pharm. Sci., 588–589). In the tests performed above, the concentration of the agent in Hank's medium therefore corresponds to the amount of said agent which would be present per dosage unit of the formulation. Thus the polysorbate 80 concentrations of 100 mg/l and 200 mg/l correspond respectively to amounts of 25 mg and 50 mg per dosage unit.

3. In vivo Evaluation of the Absorption of Compound A

Hypotension is induced in anesthetized dogs by successive i.v. administrations of [Sar$^9$,Met(O$_2$)$^{11}$] substance P at a dose ol 5 ng/kg and the inhibitory effect on this hypotension is studied by the administration of compound A in different formulations.

The intraduodenal administration of compound A in solution at a dose of 0.35 mg/kg makes it possible to re-establish the arterial pressure, whereas its administration in suspension at a dose of 0.35 mg/kg has no effect on the arterial pressure.

"Solution" is understood as meaning that compound A is in isotonic solution after being dissolved by ethanol or DMSO. "Suspension" is understood as meaning that compound A is in an aqueous solution containing 6% of methyl cellulose.

Administered orally (p.o.) at a dose of 1 mg/kg, compound A makes it possible to re-establish the arterial pressure if it is administered in solution, whereas it has no effect on the pressure if it is administered pure in a gelatin capsule.

Compound A was also administered pure in a gelatin capsule at a dose of 3 mg/kg p.o. and at a dose of 10 mg/kg p.o. The effect on the arterial pressure is small at 3 mg/kg but reaches a maximum at 10 mg/kg.

Finally, compound A formulated according to formulation 1 of the present invention was administered to anesthetized dogs at a lose of 3 mg/kg and the effect on the arterial pressure was found to be identical to that observed when compound A is administered at a dose of 1 mg/kg p.o. in solution in ethanol or DMSO.

These results show that the inhibitory effect of compound A on the hypotension induced by [Sar$^9$,Met(O$_2$)$^{11}$] substance P manifests itself only when compound A is administered in solution.

It is seen that formulation I enables the active dose of compound A to be reduced by a factor of 3. This shows the value of such a formulation for solubilizing compound A and improving its intestinal absorption.

In the present description and in the Examples which follow, the amounts of the ingredients are expressed as percentages by weight relative to the total weight of the pharmaceutical formulation.

EXAMPLE 1: Gelatin capsules

| | | |
|---|---|---|
| compound A | 3.125 mg, i.e. | 0.79% |
| lactose monohydrate | QS | 75.21% |
| corn starch | 79 mg | 20% |
| povidone K-30 | 11.85 mg | 3% |
| magnesium stearate | 3.95 mg | 1% |
| for a finished size 0 gelatin capsule containing | 395 mg | |

EXAMPLE 2: Gelatin capsules

| | | |
|---|---|---|
| compound A | 31.25 mg, i.e. | 7.9% |
| lactose monohydrate | QS | 68.1% |
| corn starch | 79 mg | 20% |
| povidone K-30 | 11.85 mg | 3% |
| magnesium stearate | 3.95 mg | 1% |
| for a finished size 0 gelatin capsule containing | 395 mg | |

EXAMPLE 3: Gelatin capsules

| | | |
|---|---|---|
| compound A | 12.5 mg, i.e. | 3.1% |
| lactose monohydrate | 262.7 mg | 66.6% |
| corn starch | 79 mg | 20% |
| povidone K-30 | 11.85 mg | 3% |
| polysorbate 80 | 25 mg | 6.3% |
| magnesium stearate | 3.95 mg | 1% |
| for a finished size 0 gelatin capsule containing | 395 mg | |

EXAMPLE 4: Gelatin capsules

| | | |
|---|---|---|
| compound A | 6.25 mg, i.e. | 1.6% |
| lactose monohydrate | QS | 69.4% |
| corn starch | 79 mg | 20% |
| polysorbate 80 | 20 mg | 5% |
| povidone K-30 | 11.85 mg | 3% |
| magnesium stearate | 3.95 mg | 1% |
| for a finished size 0 gelatin capsule containing | 395 mg | |

EXAMPLE 5: Gelatin capsules

| | | |
|---|---|---|
| compound A | 62.5 mg, i.e. | 15.6% |
| lactose monohydrate | QS | 50.3% |
| corn starch | 70 mg | 17.6% |
| polysorbate 80 | 50 mg | 12.5% |
| povidone K-30 | 12 mg | 3% |
| magnesium stearate | 4 mg | 1% |
| for a finished size 0 gelatin capsule containing | 400 mg | |

EXAMPLE 6: Gelatin capsules

| | | |
|---|---|---|
| compound A | 6.25 mg, i.e. | 1.4% |
| mannitol | QS | 89.2% |
| polysorbate 80 | 20 mg | 4.4% |
| hydroxypropyl methyl cellulose | 13.5 mg | 3% |
| crosslinked sodium carboxymethyl cellulose | 4.5 mg | 1% |
| magnesium stearate | 4.5 mg | 1% |
| for a finished size 0 gelatin capsule containing | 450 mg | |

EXAMPLE 7: Gelatin capsules

| | | |
|---|---|---|
| compound A | 62.5 mg, i.e. | 13.8% |
| mannitol | QS | 68.1% |
| polysorbate 80 | 50 mg | 11.1% |
| hydroxypropyl methyl cellulose | 22.5 mg | 5% |
| crosslinked sodium carboxymethyl cellulose | 4.5 mg | 1% |
| magnesium stearate | 4.5 mg | 1% |
| for a finished size 0 gelatin capsule containing | 450 mg | |

EXAMPLE 8: Tablets

| | | |
|---|---|---|
| compound A | 6.25 mg, i.e. | 2.1% |
| lactose monohydrate | QS | 69.7% |
| corn starch | 50 mg | 16.6% |
| povidone K-30 | 9 mg | 3% |
| polysorbate 80 | 20 mg | 6.6% |
| sodium carboxymethyl starch | 3 mg | 1% |
| magnesium stearate | 3 mg | 1% |
| for a finished tablet containing | 300 mg | |

EXAMPLE 9: Tablets

| | | |
|---|---|---|
| compound A | 6.25 mg, i.e. | 2.1% |
| lactose monohydrate | QS | 74.3% |
| povidone K-30 | 9 mg | 3% |
| polysorbate 80 | 50 mg | 16.6% |
| sodium carboxymethyl starch | 3 mg | 1% |
| anhydrous colloidal silica | 6 mg | 2% |
| magnesium stearate | 3 mg | 1% |
| for a finished tablet containing | 300 mg | |

EXAMPLE 10: Tablets

| | | |
|---|---|---|
| compound A | 62.5 mg, i.e. | 12.5% |
| lactose monohydrate | QS | 52.5% |
| corn starch | 50 mg | 10% |

-continued

| | | |
|---|---|---|
| microcrystalline cellulose | 50 mg | 10% |
| hydroxypropyl cellulose | 25 mg | 5% |
| polysorbate 80 | 20 mg | 4% |
| polyplasdone | 15 mg | 3% |
| sodium stearylfumarate | 15 mg | 3% |
| for a finished tablet containing | 500 mg | |

EXAMPLE 11: Tablets

| | | |
|---|---|---|
| compound A | 62.5 mg, i.e. | 12.5% |
| lactose monohydrate | QS | 73.9% |
| polysorbate 80 | 50 mg | 10% |
| sodium carboxymethyl starch | 3 mg | 0.6% |
| anhydrous colloidal silica | 10 mg | 2% |
| magnesium stearate | 5 mg | 1% |
| for a finished tablet containing | 500 mg | |

EXAMPLE 12: Sachets

| | | |
|---|---|---|
| compound A | 100 mg, i.e. | 10% |
| lactose monohydrate | 610 mg | 61% |
| corn starch | 200 mg | 20% |
| polysorbate 80 | 50 mg | 5% |
| crosslinked sodium carboxymethyl cellulose | 30 mg | 3% |
| magnesium stearate | 10 mg | 1% |
| for a filled sachet containing | 1000 mg | |

EXAMPLE 13: Enteric gelatin capsules

A gelatin capsule is prepared according to Example 1 and a film coating is applied in 2 layers, one a precoating layer and the other a coating layer.

Precoating:

| | |
|---|---|
| Eudragit ® L30 D-55 | 46.6% |
| glycerol | 4.6% |
| polysorbate 80 in 33% aqueous solution | 4.6% |
| water | 44.2% |

Coating:

| | |
|---|---|
| Eudragit ® L30 D-55 | 54.8% |
| glycerol | 3.3% |
| polysorbate 80 in 33% aqueous solution | 0.7% |
| water | 41.2% |

What is claimed is:

1. A pharmaceutical formulation, presented in dry form, for the oral administration of an active principle of the formula

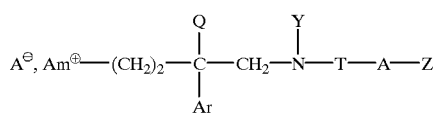

(I)

in which:

$A^{\ominus}$ is a pharmaceutically acceptable anion;

$Am^{\oplus}$ is:

i—either a group $Am_1^{\oplus}$ of the formula

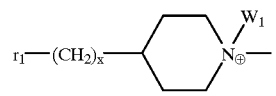

in which:

$Ar_1$ is a phenyl which is unsubstituted or monosubstituted or polysubstituted by a substituent selected from a halogen atom, a hydroxyl, a $(C_1-C_4)$alkoxy, a $(C_1-C_4)$alkyl and a trifluoromethyl, said substituents being identical or different;

x is zero or one;

$W_1$ is a $(C_1-C_6)$alkyl or a benzyl group, the substituent $W_1$ being either in the axial position or in the equatorial position;

ii—or a group $Am_2^{\oplus}$ of the formula

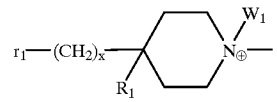

in which:

$Ar_1$, x and $W_1$ are as defined above; and $R_1$ is a hydroxyl, a $(C_1-C_4)$alkoxy, a formyloxy, a $(C_1-C_3)$alkhylcarbonyloxy, a carboxyl, a $(C_1-C_4)$alkoxycarbonyl, a cyano, a $(C_1-C_3)$alkylcarbonylamino, a mercapto or a $(C_1-C_4)$alkylthio;

iii—or a group $Am_3^{\oplus}$ of the formula

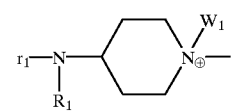

in which:

$Ar_1$ and $W_1$ are as defined above;

$R_2$ is hydrogen, a $(C_1-C_3)$alkyl, a $(C_1-C_3)$alkylcarbonyl;

iv—or a group $Am_4^{\oplus}$ of the formula

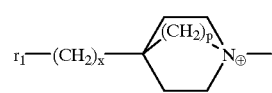

in which:

$Ar_1$ and x are as defined above; and p is one or two;

v—or a group $Am_5^{\oplus}$ of the formula

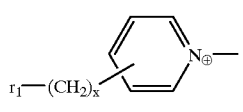

in which:

$Ar_1$ and x are as defined above;

Ar is a phenyl which is unsubstituted or monosubstituted or disubstituted by a substituent selected from a halogen atom, a $(C_1-C_3)$alkoxy, a $(C_1-C_3)$alkyl and a trifluoromethyl, said substituents being identical or different; a naphthyl; an indolyl;

Q and Y have one of the following groups of meanings:
a) $Q_1$ and $Y_1$;
b) $Q_2$ and $Y_2$ when $Am^{\oplus}$ is a group $Am_1^{\oplus}$, $Am_2^{\oplus}$, $Am_4^{\oplus}$ or $Am_5^{\oplus}$;
c) $Q_3$ and $Y_3$ when $Am^{\oplus}$ is a group $Am_1^{\oplus}$ or $Am_2^{\oplus}$ or a group $Am_4^{\oplus}$ in which $Ar_1$ is a phenyl and p is two;
d) $Q_4$ and $Y_4$ when $Am^{\oplus}$ is a group $Am_1^{\oplus}$, $Am_3^{\oplus}$, $Am_4^{\oplus}$ or $Am_5^{\oplus}$;

Q is hydrogen;

$Y_1$ is hydrogen, a $(C_1-C_4)$alkyl, an $\omega$-$(C_1-C_4)$alkoxy-$(C_2-C_4)$alkylene, an $\omega$-$(C_1-C_4)$alkylcarbonyloxy-$(C_2-C_4)$alkylene, an $\omega$-benzoyloxy-$(C_2-C_4)$alkylene, an $\omega$-hydroxy-$(C_2-C_4)$alkylene, an $\omega$-$(C_1-C_4)$alkylthio-$(C_2-C_4)$alkylene, an $\omega$-$(C_1-C_4)$ alkylcarbonyl-($C_2$–$C_4$)alkylene, an ω-carboxy-($C_2$–$C_4$) alkylene, an ω-($C_1$–$C_4$)alkoxycarbonyl-($C_2$–$C_4$) alkylene, an ω-benzyloxy-($C_2$–$C_4$)alkylene, an ω-formyloxy-($C_2$–$C_4$)alkylene, an ω-$R_3$NHCOO—($C_2$–$C_4$)alkylene, an ω-$R_4R_5$NCO—($C_2$–$C_4$)alkylene, an ω-$R_6$CONR$_7$—($C_2$–$C_4$)alkylene, an ω-$R_8$OCONR$_7$—($C_2$–$C_4$)alkylene, an ω-$R_4R_5$NCONR$_7$—($C_2$–$C_4$)alkylene, an ω-$R_9$SO$_2$NR$_7$—($C_2$–$C_4$)alkylene, an ω-cyano-($C_1$–$C_3$) alkylene;

$Q_2$ and $Y_2$ together form an ethylene, trimethylene or tetramethylene group;

$Q_3$ and $Y_3$ together form a group

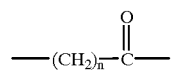

in which n is one, two or three;

$Q_4$ and $Y_4$ together form a radical selected from:
A$_1$) —O—CH$_2$—
A$_2$) —O—CO—
A$_3$) —CH$_2$—O—CO—
A$_4$) —O—CH$_2$—CO—
A$_5$) —O—CH$_2$—CH$_2$—
A$_6$) —N(R$_{10}$)—CO—
A$_7$) —N(R$_{10}$)—CO—CO—
A$_8$) —N(R$_{10}$)—CH$_2$—CH$_2$—

T is either a group —CO— when Q and Y are $Q_1$ and $Y_1$, $Q_1$ and $Y_2$ or $Q_4$ and $Y_4$ when they together form a radical A$_1$), A$_5$) or A$_8$); or a group —CH$_2$— when Q and Y are $Q_3$ and $Y_3$ or $Q_4$ and $Y_4$ when they together form a radical A$_2$), A$_3$), A$_4$), A$_6$) or A$_7$);

A is either a direct bond or a methylene group when T is —CO—, or a direct bond when T is —CH$_2$—;

Z is:
a phenyl which is unsubstituted or monosubstituted or polysubstituted by a substituent selected from a halogen atom; a trifluoromethyl; a cyano; a hydroxyl; a nitro; an amino which is unsubstituted or monosubstituted or polysubstituted by a ($C_1$–$C_4$) alkyl; a benzylamino; a carboxyl; a ($C_1$–$C_{10}$)alkyl; a ($C_3$–$C_7$)cycloalkyl which is unsubstituted or monosubstituted or polysubstituted by a methyl; a ($C_1$–$C_{10}$)alkoxy; a ($C_3$–$C_7$)cycloalkoxy which is unsubstituted or monosubstituted or polysubstituted by a methyl; a mercapto; a ($C_1$–$C_{10}$)alkylthio; a ($C_1$–$C_6$)alkylcarbonyloxy; a ($C_1$–$C_6$) alkylcarbonylamino; a benzoylamino; a ($C_1$–$C_4$) alkoxycarbonyl; a ($C_3$–$C_7$)cycloalkylcarbonyl; a carbamoyl which is unsubstituted or monosubstituted or disubstituted by a ($C_1$–$C_4$)alkyl; a ureido which is unsubstituted or monosubstituted or disubstituted in the 3-position by a ($C_1$–$C_4$)alkyl or a ($C_3$–$C_7$) cycloalkyl; and a (pyrrolidin-1-yl)carbonylamino, said substituents being identical or different;
a naphthyl which is unsubstituted or monosubstituted or polysubstituted by a halogen, a trifluoromethyl, a ($C_1$–$C_4$)alkyl, a hydroxyl or a ($C_1$–$C_4$)alkoxy;
a pyridyl; a thienyl; an indolyl; a quinolyl; a benzothienyl; an imidazolyl;

$R_3$ is a ($C_1$–$C_7$)alkyl or a phenyl;

$R_4$ and $R_5$ are each independently a hydrogen or a ($C_1$–$C_7$)alkyl; R, can also be a ($C_3$–$C_7$)cycloalkyl, a ($C_3$–$C_7$)cycloalkylmethyl, a phenyl or a benzyl; or $R_4$ and $R_5$, together with the nitrogen atom to which they are bonded, form a heterocycle selected from azetidine, pyrrolidine, piperidine, morpholine, thiomorpholine, perhydroazepine and piperazine which is unsubstituted or substituted in the 4-position by a ($C_1$–$C_4$)alkyl;

$R_6$ is a hydrogen, a ($C_1$–$C_7$)alkyl, a vinyl, a phenyl, a benzyl, a pyridyl or a ($C_3$–$C_7$)cycloalkyl which is unsubstituted or substituted by one or more methyls;

$R_7$ is a hydrogen or a ($C_1$–$C_7$)alkyl;

$R_8$ is a ($C_1$–$C_7$)alkyl or a phenyl;

$R_9$ is a ($C_1$–$C_7$)alkyl; an amino which is unsubstituted or substituted by one or two ($C_1$–$C_7$)alkyls; a phenyl which is unsubstituted or monosubstituted or polysubstituted by a substituent selected from a halogen atom, a ($C_1$–$C_7$)alkyl, a methfluoromethyl, a hydroxyl, a ($C_1$–$C_7$)alkoxy, a carboxyl, a ($C_1$–$C_7$)alkoxycarbonyl, a ($C_1$–$C_7$)alkylcarbonyloxy, a cyano, a nitro and an amino which is unsubstituted or substituted by one or two ($C_1$–$C_7$)alkyls, said substituents being identical or different;

$R_{10}$ is hydrogen or a ($C_1$–$C_4$)alkyl, or one of its salts with mineral or organic acids, if appropriate, and one of their solvates, if appropriate, formulated by wet granulation, containing the following as percentages of the total weight of the formulation:

| | |
|---|---|
| active principle | 0.5 to 50% |
| binder | 1 to 10% |
| disintegrating agent | 0 to 10% |
| antiadhesive | 0 to 5% |
| lubricant | 0.2 to 5% |
| flow promoter | 0 to 15% |
| polysorbate 80 | 4 to 20% |
| color | 0 to 2% |
| flavoring | 0 to 2% |
| diluent in sufficient amount (QS) for 100%. | |

2. A pharmaceutical formulation according to claim 1 wherein the active principle is a compound of the formula

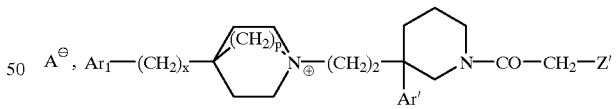

(I')

in which:

Ar$_1$, x and p are as defined for a compound of formula (I) in claim 1;

Ar' is a 3,4-dichlorophenyl or a 3,4-difluorophenyl;

Z' is a phenyl substituted in the 3-position by a halogen or a ($C_1$–$C_{10}$)alkoxy; and A$^⊖$ is a pharmaceutically acceptable anion.

3. A pharmaceutical formulation according to claim 2 wherein the active principle is (S)-1-{2-[3-(3,4-dichlorophenyl)-1-(3-isopropoxyphenylacetyl)piperidin-3-yl]ethyl}-4-phenyl-1-azoniabicyclo[2.2.2]octane of the formula

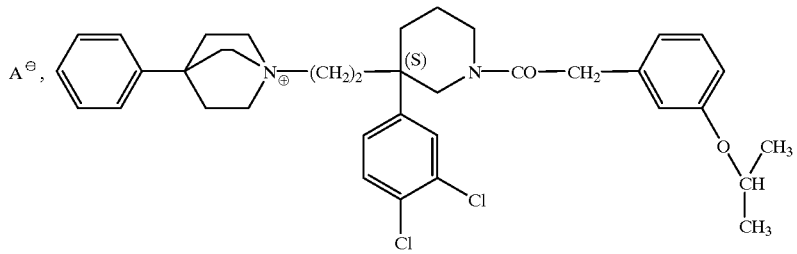

in which A⊖ is a pharmaceutically acceptable anion.

4. A pharmaceutical formulation according to claim 3 wherein the active principle is nolpitantium besilate.

5. A pharmaceutical formulation according to claim 1 wherein it contains from 15 mg to 60 mg of polysorbate 80 per dosage unit.

6. A pharmaceutical formulation according to claim 1 wherein it is presented in the form of gelatin capsules, tablets, sachets or powders.

7. A pharmaceutical formulation according to claim 1 wherein the diluent is a compound or a mixture of compounds selected from calcium phosphates, hydrated or anhydrous lactose, mannitol, microcrystalline cellulose, starch, corn starch or pregelatinized starch.

8. A pharmaceutical formulation according to claim 7 wherein the diluent is a compound or a mixture of compounds selected from lactose monohydrate, mannitol, microcrystalline cellulose and corn starch.

9. A pharmaceutical formulation according to claim 8 wherein the diluent is a mixture of lactose monohydrate and corn starch or a mixture of lactose monohydrate, coin starch and microcrystalline cellulose.

10. A pharmaceutical formulation according to claim 1 wherein the binder is a compound or a mixture of compounds selected from alginic acid, sodium alginate; cellulose, sodium carboxymethyl cellulose, ethyl cellulose, hydroxyethyl cellulose, hydroxypropyl cellulose, hydroxypropyl methyl cellulose or methyl cellulose; gelatin; acrylic acid polymers; povidone K-30.

11. A pharmaceutical formulation according to claim 10 wherein the binder is selected from hydroxypropyl methyl cellulose and povidone K-30.

12. A pharmaceutical formulation according to claim 1 wherein the disintegrating agent is a compound or a mixture of compounds selected from cellulose, sodium carboxymethyl cellulose, crosslinked sodium carboxymethyl cellulose, microcrystalline cellulose, cellulose powder or crospovidone; pregelatinized starch, sodium starch glyconate, sodium carboxymethyl starch and starch.

13. A pharmaceutical formulation according to claim 12 wherein the disintegrating agent is selected from crospovidone, crosslinked sodium carboxymethyl cellulose and sodium carboxymethyl starch.

14. A pharmaceutical formulation according to claim 1 wherein the antiadhesive is selected from silica and talcum.

15. A pharmaceutical formulation according to claim 1 wherein the flow promoter is selected from anhydrous colloidal silica and precipitated silica.

16. A pharmaceutical formulation according to claim 1 wherein the lubricant is a compound or a mixture of compounds selected from calcium stearate, glyceryl monostearate, glyceryl palmitostearate, magnesium stearate, sodium laurylsulfite, sodium stearylfumarate, zinc stearate or stearic acid; hydrogenated castor oil, polyalkylene glycols, or polyethylene glycol, sodium benzoate and talcum.

17. A pharmaceutical formulation according to claim 16 wherein the lubricant is selected from magnesium stearate and sodium stearylfumarate.

18. A pharmaceutical formulation according to claim 1 which contains:

| | |
|---|---|
| active principle | 0.5 to 20% |
| binder | 2.5 to 6% |
| disintegrating agent | 0 to 5% |
| antiadhesive | 0 to 3% |
| lubricant | 0.5 to 3% |
| flow promoter | 0 to 5% |
| polysorbate 80 | 4 to 20% |
| color | 4 to 2% |
| flavoring | 0 to 2% |
| diluent in sufficient amount (QS) for 100%. | |

19. A pharmaceutical formulation according to claim 1 which contains:

| | |
|---|---|
| nolpitantium besilate | 0.5 to 10% |
| lactose monohydrate | 60 to 80% |
| corn starch | 15 to 25% |
| povidone K-30 | 2 to 5% |
| polysorbate 80 | 4 to 20% |
| magnesium stearate | 1%. |

20. A pharmaceutical formulation according to claim 19 which contains:

| | |
|---|---|
| in the internal phase: | |
| nolpitantium besilate | 3.1% |
| lactose monohydrate | 66.6% |
| corn starch | 20% |
| povidone K-30 | 3% |
| purified water for wet granulation QS | |
| polysorbate 80 | 6.3% |
| in the external phase: | |
| magnesium stearate | 1%. |

21. A pharmaceutical formulation according to claim 1 for the preparation of enteric gelatin capsules.

22. A pharmaceutical formulation according to claim 1 for the preparation of enteric tablets.

23. A process for the preparation of pharmaceutical formulations according to claim 1 wherein:

a) for the internal phase, the active principle, the diluent and the optionally binder are mixed at room temperature;

b) the mixture is wetted with purified water;

c) the resulting wet mass is dried and graded;

d) the ingredients of the external phase, namely the lubricant, the disintegrating agent, the antiadhesive and the flow promoter, are added to the graded dry grains obtained, and in that polysorbate 80 is also incorporated, either in step a) or in step b).

24. A process according to claim 23 wherein a color is also incorporated in step a) or in step d).

25. A process according to claim 23 wherein a flavoring is also incorporated in step d).

26. A process according to claim 23 wherein the polysorbate 80 is incorporated into the purified water in step b).

27. A process according to claim 23 wherein the binder is incorporated into the purified water in step b) instead of being incorporated in step a).

28. A process according to claim 23 for the preparation of enteric formulations.

* * * * *